(12) United States Patent
Laarmann et al.

(10) Patent No.: US 8,974,767 B2
(45) Date of Patent: Mar. 10, 2015

(54) FLUORESCENT NANOPARTICLES

(75) Inventors: Sven Laarmann, Hamm (DE); Kathrin Zeller, Bad Camberg (DE); Karin Mittmann, Münster (DE); Christoph Block, Münster (DE); Claudia Arntz, Lengerich (DE)

(73) Assignee: Signalomics GmbH, Vienna (AT)

( * ) Notice: Subject to any disclaimer, the term of this patent is extended or adjusted under 35 U.S.C. 154(b) by 1211 days.

(21) Appl. No.: 12/093,977

(22) PCT Filed: Nov. 16, 2006

(86) PCT No.: PCT/EP2006/010996
§ 371 (c)(1),
(2), (4) Date: Dec. 4, 2008

(87) PCT Pub. No.: WO2007/057182
PCT Pub. Date: May 24, 2007

(65) Prior Publication Data
US 2009/0226371 A1    Sep. 10, 2009

(30) Foreign Application Priority Data

Nov. 16, 2005  (EP) .................................... 05025022

(51) Int. Cl.
| | | |
|---|---|---|
| A61K 49/00 | (2006.01) | |
| C09K 11/74 | (2006.01) | |
| C09K 11/54 | (2006.01) | |
| C09K 11/62 | (2006.01) | |
| C09K 11/56 | (2006.01) | |

(52) U.S. Cl.
CPC ............. *C09K 11/62* (2013.01); *C09K 11/7442* (2013.01); *C09K 11/54* (2013.01); *C09K 11/565* (2013.01); *A61K 49/0067* (2013.01); *C09K 11/74* (2013.01)
USPC ......................................................... 424/9.1

(58) Field of Classification Search
USPC ....................................................... 424/9.1
See application file for complete search history.

(56) References Cited

U.S. PATENT DOCUMENTS

| | | |
|---|---|---|
| 6,179,912 B1 | 1/2001 | Barbera-Guillem et al. |
| 6,207,392 B1 | 3/2001 | Weiss et al. |
| 6,306,610 B1 | 10/2001 | Bawendi et al. |
| 7,981,667 B2 | 7/2011 | Nie et al. |
| 8,088,358 B2 | 1/2012 | Haasse et al. |
| 2002/0127224 A1 | 9/2002 | Chen |
| 2004/0033345 A1 | 2/2004 | Dubertret et al. |
| 2004/0101822 A1 | 5/2004 | Wiesner et al. |
| 2004/0247861 A1 | 12/2004 | Asajima et al. |
| 2005/0112376 A1 | 5/2005 | Naasani |

FOREIGN PATENT DOCUMENTS

| | | |
|---|---|---|
| JP | 2004/530616 | 10/2004 |
| JP | 2005/513471 | 5/2005 |
| WO | WO03/054507 | 7/2003 |
| WO | WO 03054507 | 7/2003 |
| WO | WO 03062198 | 7/2003 |
| WO | WO 2004003558 | 1/2004 |
| WO | WO 2004/063387 | 7/2004 |
| WO | WO 2005/001889 | 1/2005 |
| WO | WO 2005001889 | 1/2005 |
| WO | WO 2005053649 | 6/2005 |
| WO | WO 2005081721 | 9/2005 |

OTHER PUBLICATIONS

Kircher et al., Cancer Res. 2003;63:8122-8125.*
Baker, Laboratory News, "http://www.labnews.co.uk/features/a-quantum-leap-for-in-vivo-imaging/", (Jun. 1, 2005).*
Hsu et al: "A Far-red Fluorescent Contrast Agent", in: Photochemistry and Photobiology V 79(3), 2004, pp. 272-279.
Chan et al: "Quantum Dot Bioconjugates", in: sciencemag.org V 281, 1998, pp. 2013-2016.
Stroh et al: "Quantum dots spectrally distinguish", in: Nature Medicine V 11(6), 2005, pp. 678-682.
Dubertret et al: "In Vino Imaging of Quantum Dots", in: sciencemag.org V 298, 2002, pp. 1759-1762.
Ballou et al: "Noninvasive Imaging of Quantum Dots in Mice", in: Bioconjugate Chem. V 15, 2004, pp. 79-86.
Alivisatos: "Semiconductor Clusters", in: Science V 271, 1996, pp. 933-937.
Gao et al: "In vino cancer targeting and imaging", in: Nature Biotechnology V 22(8), 2004, pp. 969-976.
Michalet et al: "Quantum Dots for Live Cells", in: sciencemag.org V 307, 2005, pp. 538-544.
Saturag et al: "Safe Levels of cadmium intake", in: British Journal of Nutrition V 84, 2000 pp. 791-802.
Bruchez M. Jr. et al: "Water-Soluble Quantum Dots", in: sciencemag.org V 300, 2003, pp. 1434-1436.
Kim, et al.: "*Near-Infrared Fluorescent Type II Quantum Dots for Sentinel Lymph Node Mapping*", Nature Biotechnology, vol. 22, No. 1, Jan. 2004, pp. 93-97 (Exhibit F attached hereto).
Tsay, et al.: "*New Light on Quantum Dot Cytotoxicity*"; Chemistry & Biology, vol. 12, Nov. 2005, pp. 1159-1161 (Exhibit H attached hereto).
Ballou, et al.: "*Noninvasive Imaging of Quantum Dots in Mice*", Bioconjugate Chem., 2004, vol. 15, No. 1, pp. 79-86 (Exhibit J attached hereto).

* cited by examiner

*Primary Examiner* — Michael G Hartley
*Assistant Examiner* — Robert Cabral
(74) *Attorney, Agent, or Firm* — Tarolli, Sundheim, Covell & Tummino LLP

(57) ABSTRACT

The use of fluorescent nanoparticles is disclosed which includes an inorganic core, a passivating layer and specific ligands having a hydrodynamic diameter of the inorganic core with the passivating layer of not more than 15 nm, preferably of not more than 10 nm, particularly preferably of not more than 5 nm, for preparing an in vivo diagnostic aid, the nanoparticles showing an emission of less than 700 nm.

18 Claims, 7 Drawing Sheets

FLUORESCENT NANOPARTICLES

CROSS-REFERENCES TO RELATED APPLICATIONS

This application is the U.S. National Stage of International Application No. PCT/EP2006/010996, filed Nov. 16, 2006, which designated the United States and has been published as International Publication No. WO 2007/057182 and which claims the priority of European Patent Application, Serial No. 05 025 022.4, filed Nov. 16, 2005, pursuant to 35 U.S.C. 119(a)-(d).

BACKGROUND OF THE INVENTION

The invention relates to fluorescent nanoparticles with particular suitability as in vivo diagnostic aid, especially as contrast agent for discriminating between different tissue types and claims the priority of European patent application 05 025 022.4, reference being made to the contents thereof.

In a large number of disorders, a diagnosis which is as early and informative as possible is crucially important for the choice and the harmonization and implementation of the necessary medical procedures. This applies in particular to a large number of tumor types, for whose determination and therapy (including possible sections) discrimination between healthy and carcinogenic tissue is essential. Accordingly, the recovery or even the survival of a patient depends crucially on whether and how well the treating and/or operating clinician can distinguish between different tissue types.

In the past, to improve diagnosis and the medical procedures, contrast agents with whose aid it is possible to visualize functions and structures in the body by imaging methods have been developed. These methods are used inter alia for targeted detection of cancer-associated cell alterations.

Thus, for example, Hsu et al. (2004) ("A far-red fluorescent contrast agent to image epidermal growth factor receptor expression", Photochemistry and Photobiology, 79 (3): 272-279) have developed a molecular-specific contrast agent based on an organic fluorophore as marker for early carcinogenic transformation. In this case, the tumor-associated overexpression of the epidermal growth factor receptor (EGFR) is utilized for identifying altered tissue in the mouth via a red fluorescent anti-EGFR antibody conjugate (Alexa660).

A general disadvantage of organic fluorophores is that they are metabolized in the body, with the fluorochrome being degraded or inactivated. The metabolization thus counteracts the high labeling intensity which is necessary for diagnosis. As the residence time of the organic fluorophore in vivo increases, this problem intensifies and represents a considerable difficulty, especially in the labeling of cells in deeper tissue layers.

In addition, organic fluorophores which emit at longer wavelengths in particular have the disadvantage that their quantum yield is reduced by the chemical conjugation process. Moreover, organic fluorophores are very susceptible to photobleaching, which may even after brief irradiation lead to a substantial loss of fluorescence. A contrast agent based on these fluorophores thus has a fluorescence strength and stability with prolonged excitation time which are too low to be suitable for the detection/labeling of cells in deeper tissue layers ("deep tissue imaging"). Thus, it is evident from the study by Hsu et al. (2004) that the Alexa660 conjugates exhibit a maximum depth of penetration of 0.5 mm, so that detection of the fluorescence is no longer a reasonable possibility.

A further known possibility for the fluorescent labeling of cellular alterations consists of using so-called quantum dots (QDs), which are fluorescent nanoparticles a few nanometers in size whose core consists of semiconductor materials such as CdSe, CdTe, InP or the like.

However, when the known QDs are used in biological systems they show the so-called blinking phenomenon, i.e. the nanoparticles alternate between a fluorescent and a non-fluorescent state. This phenomenon makes the quantum dots useless in particular for in vivo application. In addition, the "blinking" may also indicate a disintegration of the nanoparticle core, by means of which toxic cadmium may be released into the body. This is particularly disadvantageous because the quantum dots accumulate in the body, for example in the liver or the spleen.

SUMMARY OF THE INVENTION

The present invention is accordingly based on the object of providing fluorescent nanoparticles which exhibit particular suitability for use as diagnostic aid, in particular as contrast agent in vivo.

This subject is achieved as set forth in the main claim. The dependent claims and separate independent claims relate to advantageous embodiments. The nanoparticles of the invention can be employed both in vitro and in vivo for the specific labeling of selected biological structures or functions. In particular, the nanoparticles selected here can serve as in vivo contrast agents for assisting medical interventions, especially surgical interventions.

BRIEF DESCRIPTION OF THE DRAWINGS

FIG. 7a shows the BP 619 fluorescence. Cases with exlusive BP 619 fluorescenceare marked by circles. The fluorescence of the antibody A488 is shown in FIG. 7b. Some of the signals whose fluorescence is attributable exclusively to A488 have been circled. FIG. 7c represents an overlay of FIG. 7a and FIG. 7b. Many of the signals reveal a colocalization (see circles).

Figure 1:
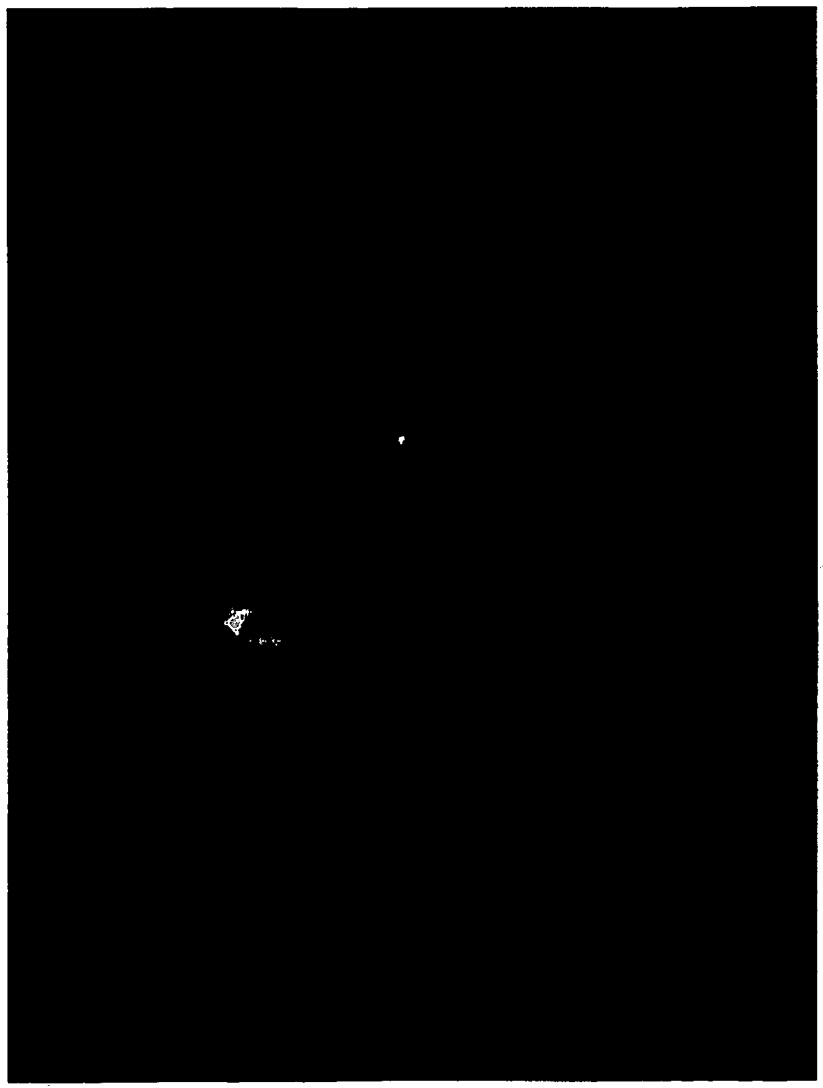
FIG. 1: Signal of a conjugate of neutravidin and biotinylated antibody against GLUT1 membrane protein due to specific binding to HT-29 cells in the direct vicinity of intratumoral ducts but not to murine cells.

The nanoparticles of the invention comprise at least three structures, specifically an inorganic core, which is sheathed by a passivating layer which then in turn carries specific ligands, it also being possible for the specific ligands to be part of the passivating layer. These lead to the specific binding of the nanoparticles to the target molecule (target) of the biological system. The inorganic core of the nanoparticles of the invention with the passivating layer surrounding it has a hydrodynamic diameter of not more than 15, preferably not more than 10 nm. thermodynamic diameters of not more than 8 nm or not more than 5 nm are particularly preferred.

The passivating layer has the task in particular of increasing the fluorescence intensity and the chemical and physical stability of the inorganic core. The inorganic cores sheathed by the passivating layer are characterized by a quantum yield of at least 10%, advantageously at least 30, 50 or even 70%. The quantum yield means in this connection the ratio of the amount of light emitted by a sample to the amount of light absorbed by the sample. The passivating layer advantageously has a thickness of not more than 1 nm. The diameter of the passivated core is in this case increased by not more than 2 nm.

It is advantageous for the nanoparticles in each case also to be provided with modifiers, in particular to improve the compatibility with the biological environment. The increase in the hydrodynamic radius through the use of modifiers preferably does not exceed 2 nm. The thickness of the passivating layer and of the modifiers depends in the individual case also on the relationships of the two structures to one another and in the relationship to the inorganic core.

Owing to the restriction on the size of the nanoparticles of the invention, they are particularly suitable for use as diagnostic aid in the living patient. Thus, the reduction in size results in an increase in the rate of diffusion and in the depth of penetration into tissue. This allows a uniform and rapid distribution of the nanoparticles in the biological environment, and penetration as far as possible through a tissue (e.g. a tumor) after local administration. The nanoparticles of the invention like-wise allow systemic administration which can also take place by injection. Local administration, e.g. topical administration or intra- or perituroral administration for the treatment of tumors, is preferred, however.

Particularly advantageous embodiments of the nanoparticles of the invention have a hydrodynamic diameter of not more than 8, particularly preferably of not more than 4 nm. Nanoparticles with a size of this order can even be excreted through the kidney, so that their accumulation in the body is distinctly less or zero. The nanoparticles of the invention thus considerably reduce the problem, which is probably associated with the known quantum dots, of long-term toxicity.

In a further advantageous embodiment, the nanoparticles of the invention emit a fluorescent spectrum between 600 and 700 nm, particularly preferably from 600 to 650 nm, especially preferably 620 to 650 nm. This emission spectrum has the advantage of maximal tissue transmission owing to only low absorption by hemoglobin and other light-absorbing substances in the living system (including water). Light of these wavelengths is still perceptible by the human eye, so that the treating clinician is able to identify the labeled tissue without further elaborate technical aids for detection (e.g. CCD cameras). This is particularly advantageous when the nanoparticles of the invention are used as contrast agents during a surgical intervention to discriminate between (for example) carcinogenic and healthy tissue.

In one embodiment, the nanoparticles which can be employed according to the invention are known nanoparticles with a core for example composed of CdSe, CdS or CdTe, as are described for example in US 2004/0247861 with reference to scientific publications (see paragraphs [0006]). Reference is also made in this publication to documents concerning the preparation of the core materials (see [0007]), e.g. to U.S. Pat. No. 6,179,912. Reference is made to these documents in their entirety for the disclosure of the properties of these known nanoparticles and the preparation thereof.

It is particularly advantageous if the inorganic core of the nanoparticles of the invention consists essentially of semiconductors. These cores emit, depending on their individual size and/or composition, light in various colors, but all show broad band absorption in the same region of the light spectrum (UV to VIS region). The excitation and emission spectra lie far apart, because of the high Stokes shift, making simple and simultaneous excitation of different quantum dots possible. They have narrow and symmetric emission spectra which overlap only slightly or not at all. Further positive properties which are of great importance in particular for the improved depth of penetration and the in vivo labeling are the high quantum yield of up to 80% and the high photostability.

Quantum dots, which may represent the inorganic core of the nanoparticles of the invention, are disclosed in WO2005/001889. According to this, an inorganic core composed of an alloy of at least two semiconductors which are either homogeneously dispersed or else for which a concentration gradient is present in each case within the alloy is involved. Reference is made to WO2005/001889 cited above concerning the disclosure of the nature and the preparation of these quantum dots. The cores may differ in size by 5% in each case.

Accordingly, the inorganic core of the nanoparticles of the invention may comprise an alloy of at least two semiconductors, the core having a homogeneous composition and being characterized by a band-gap energy which is non-linear with respect to the molar ratio of the two semiconductors.

Alternatively, the core may be non-homogeneous in nature, in which case the concentration of the first semiconductor increases gradually, starting from the center of the core, up to the surface of the core, and the concentration of the second semiconductor decreases gradually from the center of the core to the surface thereof.

It is equally true of both cores that at least one of the semiconductors is a group II-group VI semiconductor or a group III-group V semiconductor (the group definition corresponds to the groups of the Periodic Table of the Elements). The alloy may be selected for example from the group of the following alloys: CdSeTe, CdSSe, CdSTe, ZnSeTe, ZnCdTe, CdHgS, CdHgTe, InGaAs, InGaP, GaAlAs, InGaN. These cores may additionally have a coating of inorganic material such as, for example, semiconductors (e.g. ZnS). This additional layer is known to the skilled worker as "capping" or "shell".

Group II-group VI and group III-group V semiconductors are generally known and include for example $CdS_{1-x}Se_x$, $CdS_{1-x}Te_x$, $CdSe_{1-x}Te_x$, $ZnSe_{1-x}Te_x$, $Zn_{1-x}Cd_xTe$, $Cd_{1-x}Hg_xS$, $Cd_{1-x}Hg_xTe$, $In_{1-x}Ga_xAs$, $Ga_{1-x}Al_xAs$ and $In_{1-x}Ga_xP$. The semiconductors preferably used are $CdSe_{1-x}Te_x$, $CdS_{1-x}Te_x$, $ZnSe_{1-x}Te_x$, $Zn_{1-x}Cd_xTe$, $Cd_{1-x}Hg_xS$, $Cd_{1-x}Hg_xTe$, $In_{1-x}Ga_xAs$, $In_{1-x}Ga_xP$, where x is a fraction from 0 to 1.

The molar ratio of the semiconductors can assume any molar ratio. However, in the case where the alloy comprises CdSSe, a preferred alloy has the molecular formulation $CdS_{1-x}Se_x$. In the case where the alloy comprises CdSTe, a preferred alloy has the molecular formulation $CdS_{1-x}Te_x$. In the case where the alloy comprises ZnSeTe, a preferred alloy has the molecular formulation $ZnSe_{1-x}Te_x$. In the case where the alloy comprises ZnCdTe, a preferred alloy has the molecular formulation solely composed of CdTe. In these statements, x is in each case a fraction between 0 and 1.

These preferred inorganic cores of the nanoparticles of the invention can be prepared with the following steps: (i) preparation of a first solution under conditions which enable nanocrystals to form, (ii) preparation of a second solution which comprises a precursor of the semiconductors with a molar ratio under a condition which does not enable nanocrystals to form, (iii) addition of the second solution to the first solution enabling nanoparticles to form, and (iv) altering the conditions which terminate/stop the growth of the nanocrystals and the formation thereof. The method for preparing the cores is described in WO 2005/001889, to which reference is made concerning the disclosure of the preparation of this preferred embodiment of the inorganic core of the nanoparticles of the invention.

In an alternative embodiment, the inorganic core may consist essentially of a noble metal cluster which preferably comprises 2 and 27 noble metal atoms. In a preferred embodiment, the noble metal is selected from a group consisting of gold, silver, copper, platinum, palladium, osmium, iridium, ruthenium and rhodium. The cluster may have varying charges.

These cores have the advantage that, owing to their strong absorption and emission, they can easily be detected as single so-called nanodots with a weak mercury lamp excitation. The nanoparticles of the invention with these cores are advantageously to be used as fluorescent single-molecule label and mass label.

In the context of the present invention, the term "noble metal" refers to an element group selected from a group consisting of gold, silver and copper and the platinum group metals (PGM) platinum, palladium, osmium, iridium, ruthenium and rhodium. In preferred embodiments of the present invention, the noble metals are selected from the group consisting of gold, silver and copper. In a particularly preferred embodiment, the noble metal is silver or gold.

The term "cluster" refers to a combination of 2-27 atoms of a metal. Clusters are known inter alia from the areas of chemical catalysis, of ceramics, of semiconductor technology and of material sciences. The skilled worker is therefore familiar with the preparation thereof. WO2004/003558 describes inter alia the preparation of noble metal clusters and additionally contains extensive further references to the literature concerning them. There is disclosure in particular of the preparation of noble metal nanoclusters associated with organic molecules. The term association is in this connection to be understood as every type of linkage, irrespective of the chemical or physical nature of the linkage (e.g. covalent, noncovalent, electrostatic or van-der-Waals linkage). Reference is made to WO2004/003558 concerning the preparation of the nanoclusters as core of the nanoparticles of the invention.

The nanoparticles of the invention have a passivating layer which increases the fluorescence intensity and improves the chemical and physical stability of the inorganic core. The nanoparticles thus emit light preferably with a quantum yield of more than 10%, preferably of more than 50%.

The nanoparticles of the invention preferably exhibit a storage stability in an aqueous environment at 4° C. of at least 12 months and are preferably stable over a pH range from pH 5 to pH 10, i.e. they show deviations of less than 50% in relation to their specific spectral characteristics such as quantum yield, position of the emission maximum, half-width of the emission spectrum. Preferred particles show deviations of less than 10% in relation to these specific spectral characteristics.

They also show under biological conditions or in vivo essentially a constancy/stability of the properties of the core (including the passivating layer surrounding it) for a period of at least three days. Preferred particles show such a constancy/stability for a period of from 7 to 14 days or up to several weeks, where constancy means in the context of the invention a deviation/alteration of some or all of the abovementioned properties by 50%. Particularly preferred particles show a deviation/alteration of less than 10%.

The passivating layer comprises at least one compound able to coordinate metal atoms or metal ions, e.g. zinc, mercury or cadmium ions. This compound may be a Lewis base or a cyclically or linearly unsaturated compound with resonant electrons. As cyclically unsaturated compound, it may also be a heterocycle or a heteroaromatic compound. The unsaturated or conjugated group is, in a preferred embodiment, located in a terminal position in relation to the structure of the molecule. The passivating layer may further include a crosslinker, or the cyclically or linearly unsaturated compound may also function as crosslinker.

The compounds coordinating metal atoms or metal ions may bind functionally through chelation, coordination or electron donor properties of Lewis bases to fluorescent inorganic cores and correspondingly include conjugated portions/groups. These molecules may moreover comprise portions which confer solubility or wettability in aqueous solutions on the cores coated with them.

These molecules or compounds may include a homogeneous or heterogeneous (heterocyclic) ring system having one, two or more linked (or else fused) rings. Examples of preferred heteroaromatic systems are thiazoles, thiazole derivatives, oxazoles, oxazole derivatives, pyrroles, pyrrole derivatives including doped or undoped polypyrrole oligomers, thiophenes, thiophene derivatives including doped and undoped polythiophenes, furans, furan derivatives, pyridine and pyridine derivatives, pyrimidine and its derivatives, pyrazines, pyrazine derivatives, triazine and triazine derivatives, triazoles, triazole derivatives, phthalocyanines and phthalocyanine derivatives, porphyrin and porphyrin derivatives. These compounds may include unsaturated (olefinic) hydrocarbons or their amines, phosphorus derivatives or oxygen derivatives which may also include acetylene, propine and allene, but are not limited thereto. It is preferred for the molecule to have an adequate p or pi electron density in order to take part in adduct formation or resonance on the surface of the semiconductor core.

The heteroaromatic compound is preferably an imidazole component. It is further preferred for an alkylphosphine compound to be added as crosslinker.

The term "imidazole component" means in the context of this description a heterocyclic or heteroaromatic molecule which comprises at least one imidazole group (including imidazole derivatives), and which is available for the linkage of the inorganic core or of the passivating layer to a metal such as cadmium, zinc, gallium or a metal cation or a substrate which comprises such a cation. In this connection, at least one imidazole group should preferably be in a terminal position in relation to the structure of the molecule. The imidazole component binds in its functional form via the ring which comprises delocalized molecular orbitals to the fluorescent nanocrystal. The nitrogens of the imidazole ring ordinarily serve as coordinating ligands in order to bind a metal ion such as cadmium or zinc in a functional manner.

In one embodiment, the imidazole component comprises reactive functional groups such as one or two amino acid(s) e.g. histidine, carnosine, anserine, baleine, homocarnosine, histidylphenylalanine, cyclohistidylphenylalanine, 5-amino-4-imidazolecarboxamide, histidylleucine, 2-mercaptoimidazole, boc-histidine, hydrazide, histinol, 1-methylhistidine, 3-methylhistidine, imidazolysine, imidazole-containing ornithine (e.g. 5-methylimidazole), imidazole-containing alanine (e.g. (beta)-(2-imidazolyl)-L(alpha)alanine), carzinine, histamine. These histidine-based molecules or imidazole-containing amino acids can be synthesized by generally known methods.

The term "alkylphosphine" means in the context of the invention a molecule which includes at least one phosphine group (including derivatives thereof) for binding or chelating a nonmetal such as Se, S or other nonmetals, or substrates which comprise such atoms, and which provides at least one functional group (e.g. hydroxyl-, amino-, thiol-, carboxyl-, carboxamide- etc.) for reaction with adjacent molecules.

Preferably at least one phosphine group ought to be located in a terminal position in relation to the structure of the molecule. The phosphine portions serve as coordinating ligands in order to link a nonmetal or ion such as Se or S in functional form to a fluorescent core or a compound from the shielding layer.

In a preferred embodiment, the alkylphosphine-containing compound includes one, two or more phosphine groups which are coupled together (e.g. in polymeric form) and which may also include hydroxymethylphosphine compounds or the like, but are not limited thereto. Alkylphosphine-containing compounds can be synthesized by generally known methods. As is further known, alkylphosphine-containing compounds may additionally include one or more additional functional groups (e.g. hydroxyl-, amino-, thiol-, carboxyl-, carboxamide- etc.). Examples of derivatives are hydroxymethylphosphine derivatives, amides or esters, as long as the derivatization is compatible with the functions of the alkylphosphine as coating which are described herein.

Particularly preferred for coating the fluorescent inorganic cores of the nanoparticles of the invention are tris(hydroxymethyl)phosphine and β-[tris(hydroxy-methyl)phosphino]propanoic acid. It is generally known that crosslinked alkylphosphine-containing compounds have the additional possibility of binding functionally to metal atom and/or ions such as Zn or Cd. In this regard, functionalized isocyanates or alkyl cyanoacrylates may be further useful crosslinkers for ligands and adduct formation with florescent cores.

The passivating effect of the passivating layer which is present according to the invention is based on the shielding of surface cadmium or zinc atoms or the like by the complexation with the heteroaromatic compound or heterocycle (preferably with the imidazole component) and the shielding of the counter atoms (Se or S or the like) via the complexation with the alkylphosphine-containing compounds.

The passivating layer of the nanoparticles of the invention is disclosed in US 2004/0247861 A1. This published specification describes the preparation of inorganic cores sheathed with the passivating layer, for example of quantum dots. Reference is therefore made to US 2004/0247861 for the purposes of disclosing the preparation of the passivating layer employed according to the invention and of the inorganic cores sheathed therewith.

The molecules of the passivating layer may further include or carry chemical groups in order to bind and crosslink target molecules and cells (specific ligands). In the presence of corresponding passivating reagents such as $ZnSO_4$ and $Na_2S$ these molecules or compounds can form a passivating layer with the molecules on the fluorescent core ("capping" or "shell").

These reagents may also bind functionally to atoms or ions on the surface of the fluorescent nanocrystals so that this additional passivating layer can also be formed directly on the surface of the core.

The nanoparticles of the invention may, in an advantageous embodiment, additionally include modifiers which may consist of organic and/or inorganic portions. They serve to improve the compatibility, efficacy and/or solubility of the nanoparticles in a liquid or a suspending medium, in particular in the physiological environment. This surface modification is advantageous in particular in order to achieve minimal nonspecific adsorption and an increased compatibility in biological systems, especially in the human body.

One possibility is modification of the surface with the polyethylene glycol (PEG) which is already approved for certain medical applications, especially in low molecular weight forms, in order to maintain a small overall size of the nanoparticle. This can increase both the biocompatibility of the nanoparticles and the blood circulation time thereof and the efficiency of uptake into cells. By combining a low molecular weight PEG layer with further substances such as vitamins such as, for example, folic acid it is possible to achieve a smaller uptake of the nanoparticles in macrophages, because the protein adsorption to the nanoparticles is reduced thereby, thus impeding recognition of the nanoparticles by the immune system.

Coating with monosaccharides, di- or trisaccharides up to low molecular weight polysaccharides composed of one or different monosaccharides represents a further possibility for advantageous surface modification through use of modifiers. One possible embodiment is modification with, for example, polyglucose, in which it is possible to employ dextran which is approved medically as blood substitute. It shows good biocompatibility/tolerability. A further embodiment is the use of stereoisomeric forms (D-/L-) of the saccharides in order to counteract possible degradation.

A further embodiment is the use of biologically compatible hydrophilic vitamins as modifiers such as, for example, thiamine, riboflavin, niacin, pyridoxine, cobalamin, pantothenic acid, ascorbic acid and folic acid. Thus, for example, folic acid may lead to a preferred binding of nanoparticles to cancer cells. This vitamin shows only low immunogenicity and thus high biocompatibility. Binding to the membrane-associated folic acid receptor facilitates internalization of the nanoparticles.

The surface modification with lipophilic vitamins such as retinol, cholecalciferol, tocopherol and phylloquinone is likewise possible. Thus, for example, vitamin E may lead to an increased cellular uptake of nanoparticles.

Fatty acids such as, for example, 1-octadecenes or 18-methyleicosanoid acid and derivatives thereof may increase the solubility and stability of the colloids and have a terminal functional carboxyl group which can be utilized for subsequent binding of specific ligands. It is therefore worthwhile also to include fatty acids as modifiers.

A further embodiment of the surface modification is a coating with polyalcohols such as, for example, diethylene glycol (DEG) which are able particularly well to reduce nonspecific protein adsorption. The same applies to polytetrafluoroethylene (PTFE, Teflon), especially in its low molecular weight forms, on the basis of which it is possible to achieve reduced protein adsorption. Polytetrafluoroethylene is frequently employed in cardiosurgical applications.

A surface modification can likewise be undertaken with one or more naturally occurring amino acids, which include both the proteinogenic and nonproteinogenic amino acids, and synthetic amino acids. It is possible in this connection to use both stereoisomers (D and L forms). Di-, tri-, tetra-up to small polypeptides composed of the abovementioned amino acids scarcely stimulate the immune system and are thus likewise suitable for a thin compatibility layer. Possibilities in this connection are artificial amino acid sequences and sequences from biological proteins. Peptide derivatives of natural proteins such as, for example, of phytochelatin can likewise be used for surface modification. Surface modification with Tat peptide and Tat peptide-containing peptides is a further possibility for making nanoparticles available for use in biomedical applications. The Tat peptide is an efficient molecule for bringing, for example, gold nanoparticles through the cell membrane into the nucleus.

A further embodiment of the possible modifiers is the formation of a phosphorylcholine coating. Phosphorylcholine reduces possible nonspecific protein adsorption, such as, for example, on contact lenses. A phosphorylcholine modification can, because of the non-thrombogenic properties, be employed well in biological systems and is distinguished by high long-term stability.

Since polylactate is biocompatible, this substance is employed in diverse medical applications. Low molecular weight forms of polylactate in particular are a further possibility for surface modification of the nanoparticles of the invention. It is possible in this connection to employ both stereoisomers (D/L form) in order to reduce possible biodegradation.

Besides the surface modifications mentioned it is possible to link nonspecific proteins in a proteolytically cleavable manner to the nanoparticles. This may result in an increase in the biocompatibility/tolerability. Elimination of the large protein can take place at the target site to release the small nanoparticles in the tissue. It is likewise possible for the elimination to take place after an appropriate residence time. Suitable and preferred for this purpose are widely used proteins such as, for example, transferrin lactoferrin, ceruloplasmin, elastin and albumin as well as other proteins which reduce nonspecific adsorption. Thus, for example, a surface coating composed of combinations of polypeptides with elastin can prevent unwanted thrombus formation and thus increase the biocompatibility of the nanoparticles.

The main serum protein albumin is able to reduce nonspecific interactions with plasma membranes. The correspondingly modified nanoparticle moreover retains the ability of forming specific interactions with target cells through simultaneous binding of a specific ligand to the particle surface. Coating with serum albumin may lead to a substantially longer blood circulation time through the prevention of rapid uptake by macrophages after intravenous administration than is the case with uncoated nanoparticles.

Besides the nonspecific coatings outlined above, the nanoparticles of the invention carry a selective labeling with target cell-specific ligands, for example they are conjugated to proteins, antibodies, peptides or, particularly preferably, to small, high-affinity protein domains, antibody fragments or other organic molecules which bind, for example, to tumor cell-specific structures or other targets.

The combination of reduced hydrodynamic diameter, which leads to the higher rate of diffusion and perfusion mentioned, together with the previously described properties and improvements and with the high fluorescence intensity in particular in the visible red region of light makes the nanoparticles of the invention a simple diagnostic aid with diverse possible uses for selective and accurate discrimination of tissue types in vivo. These possibilities in combination with tissue-specific biomarkers serve in particular for differentiating abnormal, (pre)carcinogenic from normal tissue, assisting visual assessment for more precise tumor resection during a surgical intervention. The nanoparticles of the invention which can be employed in this connection thus serve as contrast agents.

According to the present invention, the nanoparticies can be employed either as in vitro or in vivo diagnostic aid, theranostic agent and/or therapeutic agent. They can for this purpose be administered locally (e.g. intratumorally, intramuscularly or into surgically accessible tissues/organs) or else systemically (e.g. intravenously). Local/topical administration can be envisaged as liquid, spray solution, gel, foam, cream, active patch. This may be preferred in particular for the treatment/diagnosis of hollow organs. Oral intake is also possible, e.g. as liquid or in the form of tablets or capsules. Inhalation is equally possible (e.g. spray). Anal administration by suppository is envisaged. In one variant, the nanoparticles can be implanted in depot form. The term "diagnostic aid" is used in the context of the present invention as synonym for "contrast agent", i.e. it serves for the discriminating visualization of morphological or functional structures in biological systems, especially in living people, to assist a medical intervention.

The nanoparticles can be employed as diagnostic aid especially in surgical interventions. They can likewise be used in minimally invasive methods (e.g. endoscopy, laparoscopy). Combination with imaging methods such as PET, MRI, CT etc. is worthwhile.

As already stated above, the use according to the invention in the form of local administration is particularly advantageous. The amount of Cd employed on local administration in this connection advantageously does not exceed one tenth of the total exposure which normally accumulate anyway during the course of life in the liver and kidney of a person of advanced age and usual lifestyle. The total exposure of these organs is about 18 mg (Saturag et al. 2000; "British Journal of Nutrition; 2000, (84), 791-802). Accordingly, it is advantageous on local administration for the amount of nanoparticles to be limited so that the amount of Cd supplied at least does not substantially exceed the value of 2 mg. In a particularly preferred embodiment, the tumor visualization is possible even when an amount of contrast agent which does not exceed a total amount of 0.6 mg, particularly preferably 0.2 mg, of cadmium.

The particular advantage of this embodiment is that the use of the nanoparticles in medical application on a living person is thereby possible for the first time because otherwise—i.e. as systemic administration—this is precluded because of the toxicity associated therewith. This is because local administration reduces the dose of nanoparticles necessary for adequate visualization.

It has emerged that the Cd-containing contrast agent is advantageously employed according to the invention for visualizing a tumor in vivo in a dose corresponding to an amount of from 0.002 to 0.02 mg of Cd per $cm^3$ of tumor tissue. Dosages of the contrast agent of from 0.002 to 0.015 mg of Cd/$cm^3$ of tumor tissue are particularly advantageous, in particular between 0.002 and 0.010 mg of Cd/$cm^3$. It is possible with this advantageous dosage to visualize tumors with a volume of up to about 150 $cm^3$ in vivo without thereby exceeding the normally acceptable upper limit of exposure for humans.

The investigations may relate to all accessible tissues/organs of the patient, especially the skin, hollow organs (e.g. in the gastrointestinal, urogenital, respiratory tract) or else externally accessible regions of the sensory organs and also the cardiovascular system.

Use as in vitro diagnostic aid is also possible, e.g. immunohistochemistry or FACS, and ELISA. A combination of in vivo and in vitro diagnosis (e.g. biopsy material) is particularly advantageous.

Where the nanoparticles are employed according to the invention for therapeutic purposes, only some of the ligands of the nanoparticle may carry effector molecules or active substances, i.e. represent effectors. An effector in this connection is a ligand with a selected function. The nanoparticle advantageously carries both specific ligands for targeted localization of the nanoparticle in the body or in the tissue, and a ligand with effector molecule.

The effector may remain linked to the nanoparticle or be able to be eliminated, or detached or released. The effector may for example exert its function via an activation/inactivation of a receptor, a masking of (surface) structures, activation of the immune system ("priming"), modulation of signaling pathways, activation or deactivation of an enzyme, gene therapy (e.g. by targeted delivery of plasmids or siRNA), targeted delivery of toxins/chemotherapeutics/cytostatics or a stimulating effect on, for example, metabolism, hormone production inter alia. Protection of cells, e.g. insulin-producing B cells, is also possible.

1. Methods
a) Preparation of a BP619-neutravidin Conjugate with Linked Biotinylated Monoclonal Antibody
Chemicals and Materials
Nanoparticles
BP619 200 µg/ml The BP619 or BP617 nanoparticle is a nanoparticle of the invention, i.e. it has a $CdS_xS_e$ core ("alloy core") and a passivating layer as disclosed in US 2004/0247861 A1.
Protein Purified protein is present in phosphate/NaCl buffer (storage at −80° C.)

MES buffer substance (Sigma), NaCl, KCl, $Na_2HPO_4$, $KH_2PO_4$, EDC (1-ethyl-3-[3-dimethylaminopropyl]carbodiimide hydrochloride), S-NHS (N-hydroxysulfosuccinimide), dialysis chambers (Slide-A-Lyzer), Vivaspin (MWCO 50 kDa, VivaScience)
Buffer
D-PBS (10×)
1370 mM NaCl (80 g/l)
27 mM KCl (2 g/l)
42 mM $Na_2HPO_4*12H_2O$ (15.4 g/l)/7.652 g/l $Na_2HPO_4.2H_2O$
14 mM $KH_2PO_4$ (2 g/l)
make up to 1000 ml, the pH should be about 7.5, autoclave, storage at RT.

For a 1×PBS solution, dilute 100 ml of 10× buffer with $ddH_2O$ and, before making up completely to 1 l, adjust the desired pH (pH 7.4 (Ab) or 8.0 (QD)) with a few drops of 2 M NaOH.
MES buffer=activation buffer
Make up fresh (organic buffer, cannot be autoclaved)
Formula for 0.8 l (0.1 M MES, 0.25 M NaCl, pH 6.0):
15.616 g MES
11.688 g NaCl
ad 800 ml $ddH_2O$, adjust pH 6.0
Make up to a maximum of 0.7 l with $ddH_2O$, then adjust the pH with 2 M or 5 M NaOH. Subsequently make up to 800 ml with $ddH_2O$.

1 M lysine solution (can be stored for a lengthy period at 4° C. if sterilized by filtration), frees aliquots Procedure Firstly, MES buffer (activation buffer) is prepared in a glass measuring cylinder. The dialysis chamber is hydrated in MES buffer for 1 to 2 minutes before use. 100 µl of BP619 (20 µg) are made up to a final volume of 400 µl with MES buffer in a sterile Expender vial and thoroughly mixed with a pipette. The BP619 are transferred into the dialysis chamber (3.5 kDa). In the first dialysis, the BP619 are dialyzed against 800 ml of MES activation buffer at room temperature with continuous mixing and protecting from light for one hour. After the first dialysis, the BP619 are removed from the dialysis chamber and transferred into an Expender vial. For mixing EDC and S-NHS with the BP619, stock solutions of in each case 100 mM EDC and 100 mM S-NHS are prepared immediately before use. After the first dialysis, 33 µl of 100 mM S-NHS and 13 µl of 100 mM EDC are pipette into the BP619 and shaken at room temperature and 350 rpm, protecting from light, for 15 minutes. After the incubation, the BP619 are dialyzed against PBS. For this purpose, the BP619 are transferred into the dialysis chamber (MWCO 3.5 kDa) and dialyzed against PBS with pH 8.0, protecting from light, for one hour. After the second dialysis, the BP619 are removed from the dialysis chamber and transferred into an Expender vial. The activated BP619 are mixed with 80 µg of neutravidin (8 µl at 10 mg/ml, 20 µl final volume with D-PBS). This reaction mixture is then shaken at room temperature and at 350 rpm, protecting from light, for 2 hours. After the conjugation, the conjugation mixture is stored at 4° C., protecting from light. The following day, 1 M lysine is pipette in to a final lysine concentration of 10 mM in order to saturate any reactive groups still present.

The BP619 conjugates are concentrated using Vivaspin centrifuge tubes. The conjugates are centrifuged until the desired concentration is reached. This is followed by stoichiometric addition of biotinylated monoclonal antibody directed against the membrane-associated and tumor-associated glucose transporter 1 (GLUT1) antigen.

b) Conjugation of BP619 with EGF-His
Chemicals and Materials
Nanoparticles
BP619 200 µg/ml
Protein
Purified protein is present in phosphate/NaCl buffer (storage at −80° C.)

MES buffer substance (Sigma), NaCl, KCl, $Na_2HPO_4$, $KH_2PO_4$, EDC (1-ethyl-3-[3-dimethylaminopropyl]carbodiimide hydrochloride), S-NHS (N-hydroxysulfosuccinimide), dialysis chambers (Slide-A-Lyzer), Vivaspin (MWCO 50 kDa, VivaScience)
Buffer
D-PBS (10×)
1370 mM NaCl (80 g/l)
27 mM KCl (2 g/l)
42 mM $Na_2HPO_4*12H_2O$ (15.4 g/l)/7.652 g/l $Na_2HPO_4.2H_2O$
14 mM $KH_2PO_4$ (2 g/l)
make up to 1000 ml, the pH should be about 7.5, autoclave, storage at RT.

For a 1×PBS solution, dilute 100 ml of 10× buffer with $ddH_2O$ and, before making up completely to 1 l, adjust the desired pH (pH 7.4 (Ab) or 8.0 (QD)) with a few drops of 2 M NaOH.
MES buffer=activation buffer
Make up fresh (organic buffer, cannot be autoclaved)
Formula for 0.8 l (0.1 M MES, 0.25 M NaCl, pH 6.0):
15.616 g MES
11.688 g NaCl ad 800 ml ddH$_2$O, adjust pH 6.0

Make up to a maximum of 0.7 l with ddH$_2$O, then adjust the pH with 2 M or 5 M NaOH. Subsequently make up to 800 ml with ddH$_2$O.

1 M glycine solution (can be stored for a lengthy period at 4° C. if sterilized by filtration), frees aliquots Procedure Firstly, MES buffer (activation buffer) is prepared in a glass measuring cylinder. The dialysis chamber (3.5 kDa) is hydrated in MES buffer for 1 to 2 minutes before use. 100 µl of BP619 (20 µg) are made up to a final volume of 400 µl with MES buffer in a sterile Eppendorf vial and thoroughly mixed with a pipette. The BP619 are transferred into the dialysis chamber (3.5 kDa). In the first dialysis, the BP619 are dialyzed against 800 ml of MES activation buffer at room temperature with continuous mixing and protecting from light for one hour. After the first dialysis, the BP619 are removed from the dialysis chamber and transferred into an Eppendorf vial. For mixing EDC and S-NHS with the BP619, stock solutions of in each case 100 mM EDC and 100 mM S-NHS are prepared immediately before use. After the first dialysis, 33 µl of 100 mM S-NHS and 13 µl of 100 mM EDC are pipetted into the BP619 and shaken at room temperature and 350 rpm, protecting from light, for 15 minutes. After the incubation, the BP619 are dialyzed against PBS. For this purpose, the BP619 are transferred into the dialysis chamber (3.5 kDa) and dialyzed against PBS with pH 8.0, protecting from light, for one hour. After the second dialysis, the BP619 are removed from the dialysis chamber and transferred into an Eppendorf vial. The activated BP619 are conjugated with 4.92 µg of EGF-His (diluted with PBS to a final volume of 20 µl). For this purpose, the activated BP619 are pipetted into EGF-His and thoroughly mixed with the pipette. This reaction mixture is then shaken at room temperature and at 350 rpm, protecting from light, for 2 hours. After the conjugation, the conjugation mixture is stored at 4° C., protecting from light. The following day, 1 M glycine is pipetted in to a final glycine concentration of 10 mM in order to saturate any reactive groups still present.

The BP619-EGF-His conjugates are concentrated using Vivaspin centrifuge tubes (50 kDa MWCO). In this case, the membrane is prewashed once with 4 ml of ddH2O and then washed again with 4 ml of PBS. The BP619-EGF-His conjugates are diluted in 2 ml of PBS and loaded onto the membrane. The BP619-EGF-His conjugates are then washed again with 2 ml of PBS. The conjugates are centrifuged until the desired concentration is reached.

c) Animal Experiment

Procedure

For this purpose, human colon carcinoma cells of the HT29 cell line were injected subcutaneously into nude mice (without thymus and therefore immunosuppressed) and formed solid tumors after a growth time of about 2 to 3 weeks.

Each mouse is anesthetized with Hypnomidate in order to undertake the injection and is injected intratumorally with 25 µl of a nanoparticle solution; the injection in this case takes place centrally at one site in the tumor.

Kinetics of the fluorescence of the material in the tumor are recorded from time 0 to 5 and 60 min.

After sacrifice, firstly the tumor with epidermis is removed and then the organs spleen, liver, kidneys are removed.

The tumor is removed with epidermis-dermis, frozen with one drop of OCT on aluminum foil (outside pointing upwards), packed in aluminum foil and shock-frozen in N$_2$. Then stored at −80° C. until transported back on dry ice, further storage at −80° C.

The organs spleen, liver, kidneys are removed from all the mice, shock-frozen in N$_2$ and stored at −80° C. until transported back.

ii) Photographic Documentation

Materials/Equipment Used

Nikon Coolpix P2 camera

24 W cold light source (Eltrotec LB24)

Optical filters:

Shortpass filter 50% cutoff wavelength 550 nm (Melles Geriot 03SWP408 or 03SWP608)

"Green" color filter 550 nm (Melles Geriot 03FCG087/OG550)

"Orange" color filter 570 nm (Melles Geriot 03FCG089/OG570)

"Red" color filter 590 nm (Melles Geriot 03FCGO98/OG590) black clay board as background.

Camera Settings

The photographs to document the fluorescence are taken with a commercially available digital compact camera (Nikon Coolpix P2). The settings made on the camera are summarized below.

| Setting | Value |
| --- | --- |
| White balance (WB) | "Direct sunlight" (fixed) |
| Exposure metering | "Spot metering" |
| Continuous shooting | "Single image" |
| Best shot selector | "Off" |
| Bracketing | "Bracketing" |
| Flash compensation | "0" |
| Contrast | "Normal" |
| Sharpening | "Off" |
| Color saturation | "+/−0" |
| ISO sensitivity | 64 |
| Image quality | "fine" |
| Image size | "2592 × 1944" |
| Compression | "Medium" |
| Autofocus | "single autofocus" |
| Fixed aperture | "On" |
| Noise reduction | "Off" |
| Exposure compensation | Variable (std. −2) |

The respective image settings can be taken from the EXIF information in the image file (e.g. with Photoshop or PixVue).

Procedure

The camera is mounted with the filter holder on a tripod and adjusted with the aid of the 3D head so that the distance between lens and mouse/surface is about 15-20 cm. The angle should be as steep as possible from above, as far as permitted by the positioning of the tripod. The photographic filter is mounted so that the distance from the lens is as small as possible.

The illumination and excitation of the substance takes place by a cold light source whose spectrum is controlled by a short pass filter (see above). Because of the heat produced by the light source and to improve manipulability, a flexible light guide with a lens is used to focus the light cone. The filter holder with the short pass filter is mounted on this light guide. The light guide is then fixed in a laboratory stand so that the distance to the surface is about 15 cm. The light cone should moreover be adjusted so that its diameter is about 8 cm. The angle of illumination from above should moreover be as steep as possible to reduce shadows.

The mouse and the laboratory stand for the illumination are positioned on black clay board to improve the contrast. The mouse is then positioned in the middle of the light cone. Care should be taken in this connection that the tumor produces minimal shadow and is well lighted.

The autofocus display should be noted when the photograph is taken.

The photographs should be taken in the normal case with the maximum wide angle. With relatively large zoom the camera may become unfocused and, in addition, the aperture setting changes.

If the photographic filter is changed between photographs, if possible nothing else should be changed in the experimental setup in order to ensure comparability and facilitate later processing.

d) Cell-binding Assay

Materials and Equipment

Fluorescence microscope: Leica DMIL, Zeiss LSM510META
Signal enhancer, ProLong Gold Antifading Reagent
Buffer
D-PBS (pH 7.4) (10×)
1. 1370 mM NaCl (80 g/l)
2. 27 mM KCl (2 g/l)
3. 42 mM $Na_2HPO_4*12H_2O$ (15.4 g/l)/7.652 g/l $Na_2HPO_4*2H_2O$
4. 14 mM $KH_2PO_4$ (2 g/l)
Adjust pH 7.4 and make up to 1000 ml
autoclave, storage at RT
Triton X-100 solution
0.1% (v/v) in D-PBS
Storage at 4° C.
BSA solution
3% (w/v) in D-PBS
Make up fresh or from −20° C. stock
4% PFA solution
5. 5.71 ml of formaldehyde (35%)
6. 5 ml of 10× D-PBS
7. adjust/check pH 7.4
ad 50 ml with $ddH_2O$, storage at 4° C.
8. M glycine solution
9. 0.375 g of glycine
ad 50 ml D-PBS, adjust/check pH 7.4, sterilize by filtration, storage at 4° C.
Mowiol/DABCO Mixing of 2.4 g of Mowiol in 6 g of glycerol (extra pure) is followed by addition of 6 ml of $ddH_2O$ and then stirring at RT for several h. 12 ml of 0.2 M tris (pH 8.5) are added thereto, and the mixture is heated at 50° C. with stirring for 10 min. After the Mowiol has dissolved (takes longer than 10 min), the mixture is centrifuged at 5000×g for 15 min and finally 20 mg/ml DABCO are added.

Storage: in aliquots at −20° C., can be used for only a few weeks at 4° C., slowly hardens Antibodies First antibody: Anti-EGFR mAb (mouse) Dianova Ab-5 1:100
Second antibody: goat anti-mouse with Alexa488

Procedure 2 days beforehand, HT29 cells are seeded on circular coverslips. For the seeding, $5 \times 10^4$ cells are transferred so that, after growth at 37° C. for 48 hours, a 50-70% confluent monolayer is present at the start of the immunostaining.

The BP619-EGF-His conjugates are preincubated in 50 µl of McCoy medium containing 3% BSA at room temperature for 30 minutes.

When the HT29 cells reach confluence, the medium is aspirated off and the cells are washed at least once with D-PBS.

30 to 50 µl of the preincubated BP619-EGF-His conjugates are pipetted onto the washed cells and then incubated in an incubator at 37° C./7.5% $CO_2$ for one hour.

After the cells have been stained with the BP619-EGF-His conjugates, the cells are washed once with PBS and then fixed with 300 µl of 4% PFA solution at room temperature for 15 to 20 minutes. After the fixation, the cells are washed once with D-PBS and quenched with 0.1 M glycine at room temperature for 5 minutes. After the quenching, the cells are washed once with D-PBS and then permeabilized with 0.1% Triton X-100-PBS at room temperature for 10 minutes. The cells are blocked by subsequently incubating the cells with 3% BSA at room temperature for 30 minutes.

After blocking of the stained cells, the cells can be counterstained or the BP619-EGF-His conjugate staining can be analyzed directly under a microscope. Counterstaining is necessary to analyze the colocalization.

The counterstaining is done with the first antibody, anti-EGFR, a monoclonal antibody from Dianova. The anti-EGFR antibody is diluted 1:100 in 30 µl of 1% BSA-PBS and then pipetted onto the cells. Anti-EGFR incubates on the cells at room temperature for 60 minutes. After the incubation, the cells are washed with D-PBS for 3×5 minutes. The second antibody with fluorochrome for the counterstaining is goat anti-mouse with Alexa488. For this purpose, the second antibody is diluted 1:200 in 30 µl of 1% BSA and then pipetted onto the cells. The goat anti-mouse Alexa488 second antibody is incubated on the cells at room temperature for 60 minutes. After the incubation, the cells are washed with D-PBS for 3×5 minutes. The cells are embedded in Mowiol/DABCO and analyzed under a microscope.

e) Preparation and Staining of Cryo Sections

The tumors are stored at −80° C. and transported in a Styropor box with cooling units (cooled to −80° C.) for sectioning. The sectioning takes place with a cry-microtome. The resulting sections are 10 µm thick.

Materials and Equipment

Fluorescence microscope: Leica DMIL, Zeiss LSM510META, troughs for washing, humidity chamber, grease pen for marking the tissue region, 4% strength paraformaldehyde solution (see cell-binding assay), PBS (see cell-binding assay), 3% strength BSA solution (see cell-binding assay), Triton X-100 solution (see cell-binding assay), 0.1 M glycine solution (see cell-binding assay)

Appropriate primary and secondary antibodies, where appropriate further reagents for counterstaining Procedure The cryo sections are thawed at RT and dried (about 10-20 min). After the tissue region has been marked with a grease pen, the tissue is fixed with 4% strength paraformaldehyde solution in a humidity chamber for 20 min. After washing with D-PBS subsequently quenching with 0.1 M glycine solution for 5 min.

Washing in PBS and permeabilization with 0.1% Triton X-100 are followed by blocking with 3% strength BSA solution at RT for 1 h.

An anti-EGFR-A488 direct conjugate is used for detecting EGFR in the plasma membrane. This conjugate is diluted 1:100 in 1% BSA/PBS, and the sections are incubated therewith in a humidity chamber at RT for 1 h. Washing with D-PBS takes place in a trough for at least 15 min with at least one buffer change.

Mowiol/DABCO is employed for the embedding, and the sections (unstained and stained) are analyzed under a microscope.

f) Microscopic Analysis

The microscopic analysis of the specimens takes place with a Zeiss LSM510. The following filters are employed for this purpose:

for NP fluorescence analysis:
FSet 15=FilterSet 15 488015-0000
Excitation: BP546
Beamsplitter: FT580
Emission: LP 590
for Alexa488 fluorescence analysis:
FSet 46=FilterSet 46 1196-681
Excitation: BP500/20
Beamsplitter: FT515
Emission: BP535130

DETAILED DESCRIPTION OF PREFERRED EMBODIMENTS

A confocal laser analysis was also carried out with some of the specimens (see instructions for operating the microscope).

2. Exemplary Embodiments a) Exemplary Embodiment 1:

In vivo Experiment: Animal Experiment with HT29 Xenograft Tumors in Nude Mice with Intratumoral Injection of Neutravidin-antibody Complexes According to the Invention A specific tumor targeting of antibody conjugates according to the invention was shown in an in vivo experiment on mice with xenograft tumors. For this purpose, human colon carcinoma cells of the HT29 cell line were injected subcutaneously into nude mice (without thymus and therefore immunosuppressed) and formed solid tumors after a growth period of 3 weeks.

For a selective tumor marking, an antibody complex according to the invention was prepared, or a neutravidin conjugate according to the invention with a biotinylated monoclonal antibody linked thereto. This monoclonal antibody is directed against the membrane-associated tumor-associated glucose transporter 1 antigen (GLUT1) which is expressed on many types of human colorectal carcinomas.

After intratumoral injection of the complexes, the tumors were immediately identifiable visually by red fluorescence with UV excitation. After up to 48 h after injection it was possible to detect the complexes of the invention in the prepared cryo sections of the tumors.

FIG. 1: Red signal (conjugate of neutravidin and biotinylated antibody against GLUT1 membrane protein). Specific binding to HT-29 cells but not to murine cells is evident (homogeneous marking of the complete tumor not yet achieved).

Figure 2:
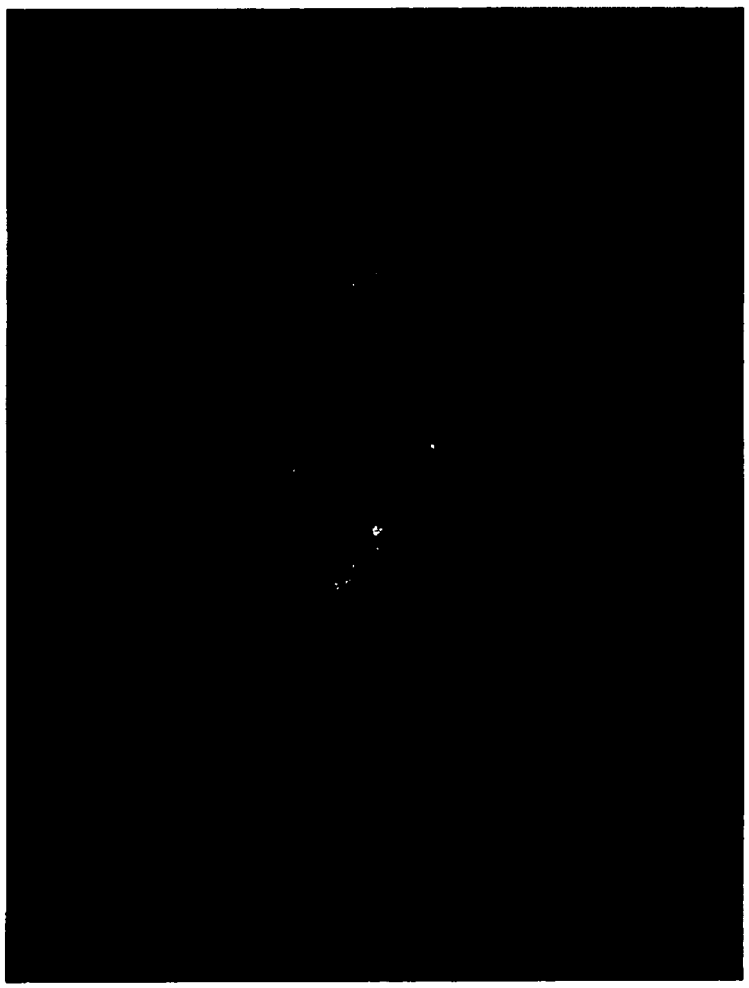
FIG. 2: Signal of a conjugate of neutravidin and biotinylated antibody against GLUT1 membrane protein due to specific binding to HT-29 cells in the direct vicinity of intratumoral ducts but not to murine cells.

FIG. 2: Red signal (conjugate of neutravidin and biotinylated antibody against GLUT1 membrane protein). Specific binding to HT-29 cells in the direct vicinity of intratumoral ducts but not to murine cells is evident. (Homogeneous marking of the complete tumor not yet achieved).

b) Exemplary Embodiment 2:

Comparison of the intensity of Biopixels 618 (material according to the invention) with Crystalplex alloy nanoparticles 630 (NC 630) by spectral analysis. The NC630 nanoparticles are nanoparticles having a $CdS_xS_{e1-x}/Zn5$ core and functionalized with COOH groups.

Figure 3:
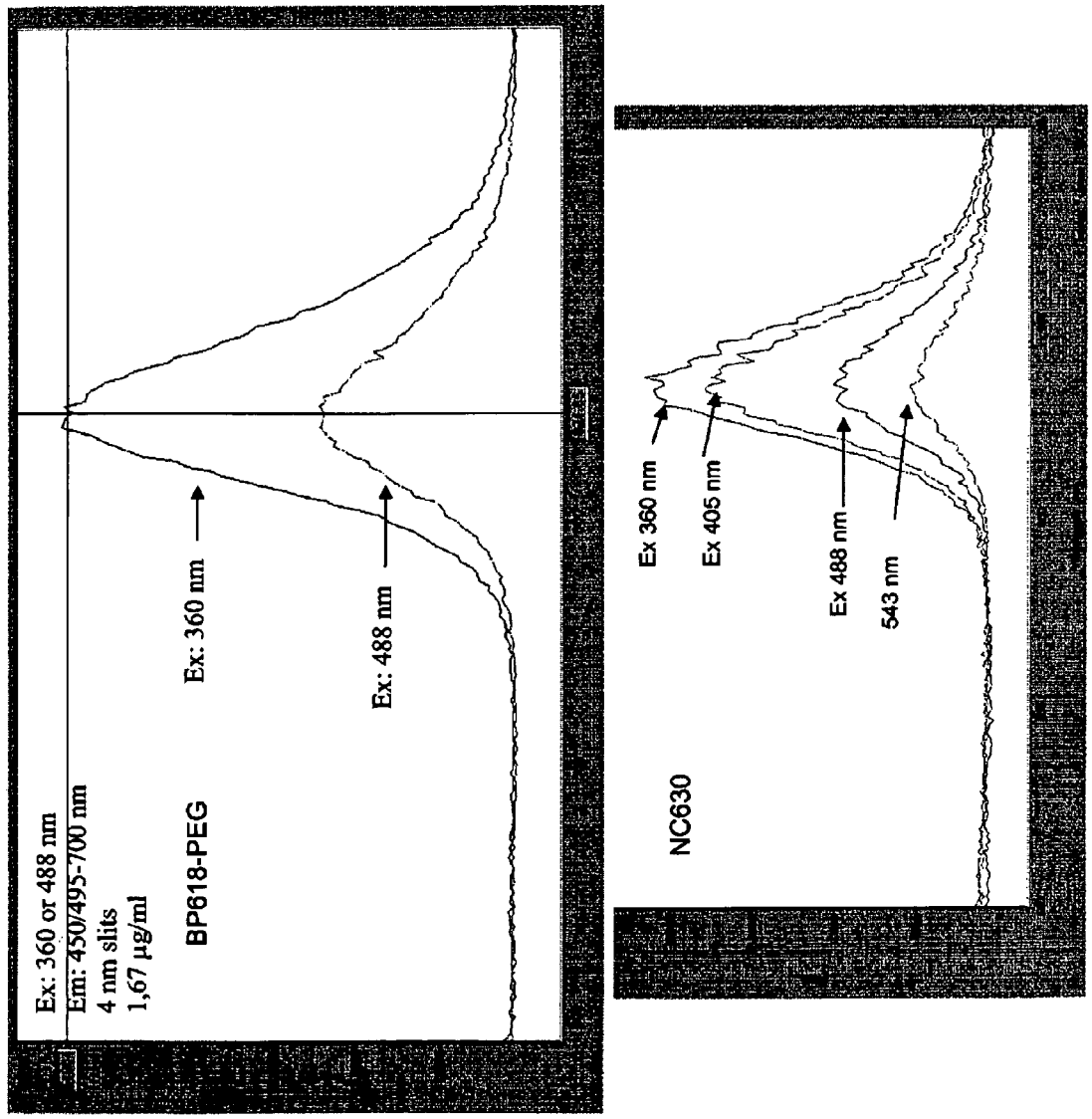
FIG. 3: Comparison of the intensity of Biopixels 618 (material according to the invention, graph in top) with Crystalplex alloy nanoparticles 630 (NC 630; graph in bottom) by spectral analysis.

The following values are evident from FIG. 3:

| | |
|---|---|
| BP618 concentration | 1.67 µg/ml |
| NC630 concentration | 6.70 µg/ml |
| BP618 excitation 360 nm | 55 000 cps |
| NC630 excitation 360 nm | 22 000 cps |
| BP618 excitation 488 nm | 25 000 cps |
| NC630 excitation 488 nm | 10 000 cps |

When the higher concentration, by a factor of 4, of the NC630 nanoparticles is taken into account, the emission intensity of the BP618 material of the invention is a factor of 10 higher.

This difference in intensity is very essential for the use according to the invention of the contrast agent for direct visualization, e.g. on medical application in surgery. Whereas with the material of the invention it is possible for the treating clinician to observe the fluorescence directly and merely with the aid of fluorescence filters, the NC630 nanoparticles would need additional electronic amplification to be made visible.

ii) Characterization of the BioPixels 619 by Gel Filtration

Figure 4:
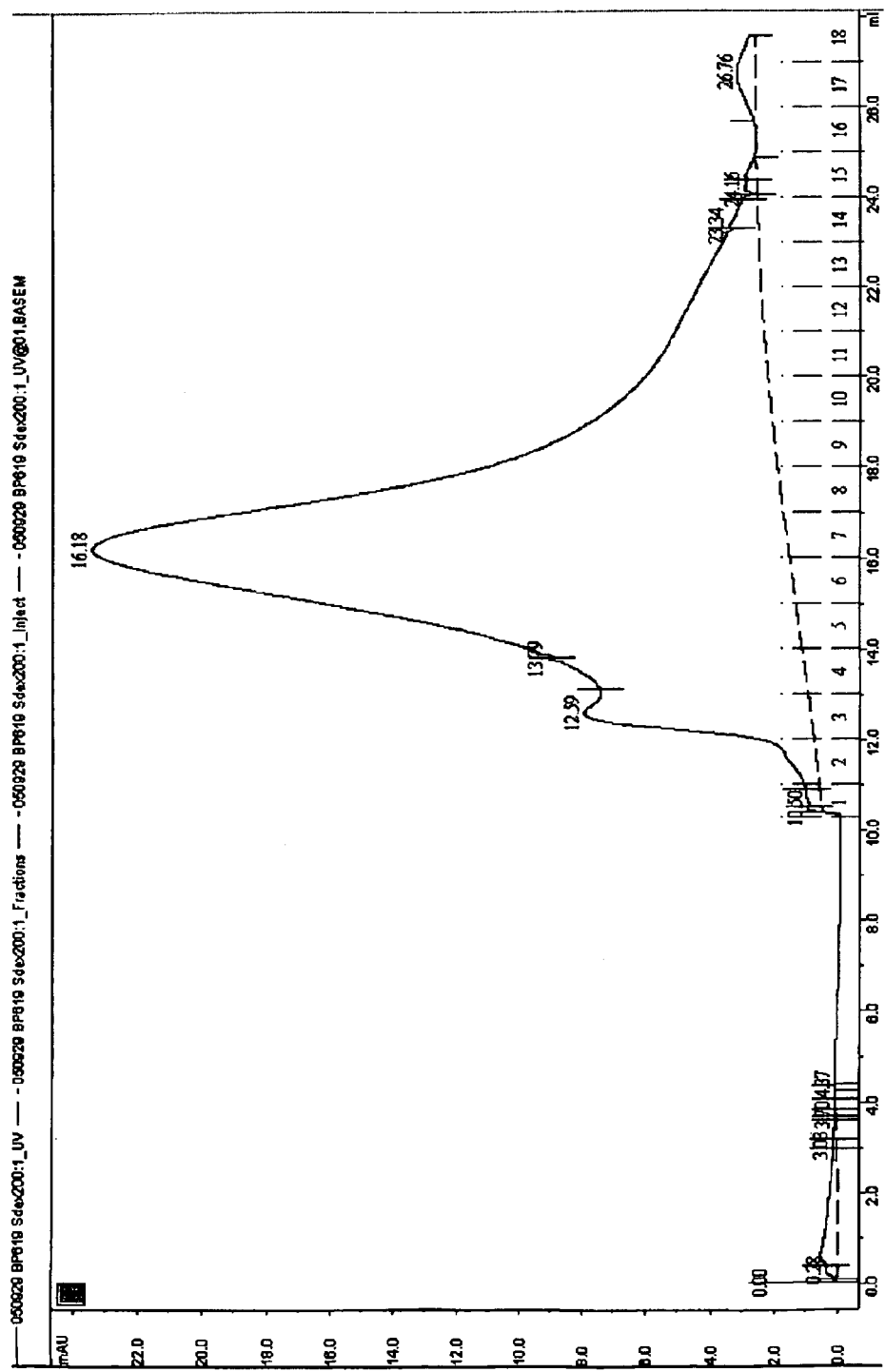
FIG. 4: Characterization of the Biopixels 619 by gel filtration exhibiting an elution volume of 16.2.ml which correlates to a Stokes diameter of 10.8 nm.

FIG. 4 reveals that the elution volume is 16.2 ml. This value correlates with a Stokes diameter of 10.8 nm.

iii) Comparison of Mouse Tumor after Injection of EGF-coupled
BioPixels 619 NC630 nanoparticles Conjugation of BP619 with EGF-His was carried out by the method described under 1b). In this case, 1.4 µM protein were employed, and 40 µg of nanoparticles (=duplicate) were conjugated. After purification/concentration with Vivaspin centrifuge units, a total of about 14.3 µg of nanoparticles were injected into the tumor.

Figure 5:
FIGS. 5a-b: Photographic documentation of mouse tumor after injection of EGF-coupled BioPixel 619 in 5a) or NC630 nanoparticles in 5b). The tumors in which the NC630 nanoparticle material was injected showed no fluorescence (FIG. 5a, see marking) whereas on use of EGF-coupled Biopixels 619 of the invention a fluorescence is distinctly evident (FIG. 5b, see marking).
Figure 6:
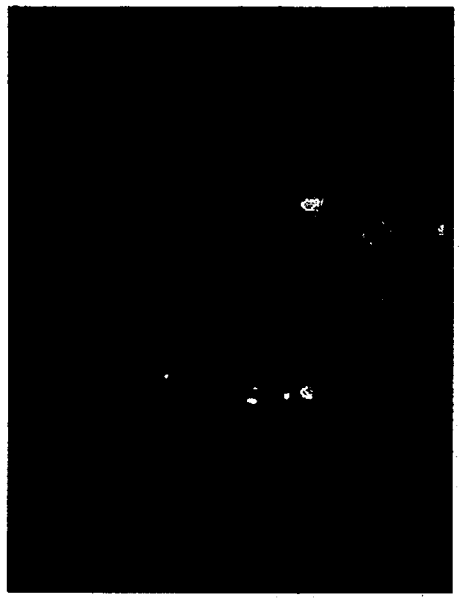
FIGS. 6a-b: Microscopic analysis of the tissue marking in the tumor who EGF-coupled Biopixels 619 of the invention. The marking of the tumor is not homogenous; some areas are marked less strongly (see FIG. 6a), whereas other show stronger marking (see FIG. 6b).
Figure 6:
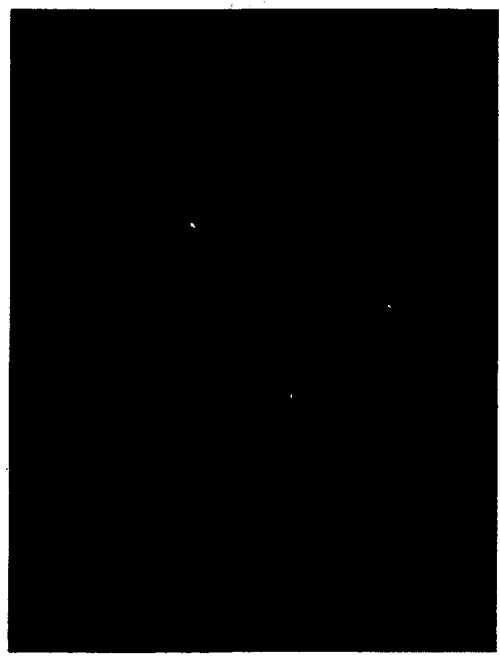

Photographic documentation took place as described under 1c). The tumors into which the NC630 material was injected showed no fluorescence (FIG. 5a, see marking), whereas on use of EGF-coupled BioPixels 619 of the invention a fluorescence is distinctly evident (FIG. 5b, see marking).

iv) Microscopy of the Tissue Marking in the Tumor with EGF-coupled BioPixels 619 of the Invention The removed tumors were sectioned using a cryotome (section thickness 10 µm) and treated for microscopic analysis as described above (1e). The analysis took place with a Zeiss microscope (LSM510) using the FSet15 for detecting the BioPixel fluorescence (see 1f). The marking of the tumor (see FIG. 6; white areas on a dark background) is not homogeneous; some areas are marked less strongly (see FIG. 6a), where others show stronger marking (see FIG. 6b).

c) Exemplary Embodiment 3

Marking of tumor cells with EGF coupled BioPixels 619 of the invention with intracellular uptake of the biopixels.

Figure 7:
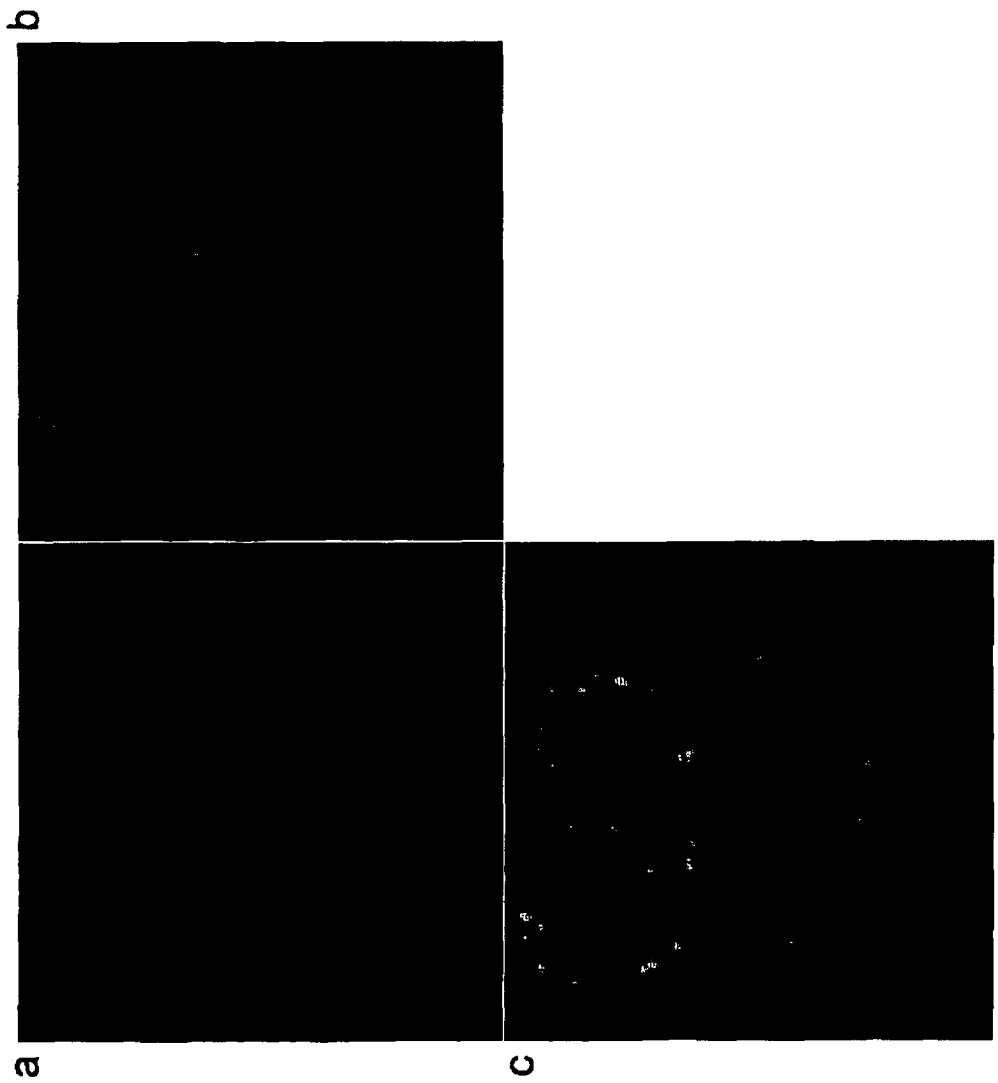
FIGS. 7a-c: Marking of HT29 tumor cells with EGF-coupled BioPixels 619 with intracellular uptake of the Biopixels.

In this case, a cell-binding assay was carried out with HT29 tumor cells by the method described (1d). FIG. 7a shows the BP619 fluorescence. In this case, some of the signals whose fluorescence is caused exclusively by BP619 have been marked by circles. The fluorescence of the antibody A488 was detected in FIG. 7b. The first antibody employed here was an EGFR antibody and the second antibody was goat anti-mouse A488 (see 1d). Once again, some of the signals whose fluorescence is attributable exclusively to A488 have been circled. Finally, FIG. 7c shows the picture copied together from 7a and 7b. Many of the signals reveal a colocalization, i.e. they are to be found both on FIG. 7a and FIG. 7b.

The invention claimed is:

1. A method of using fluorescent nanoparticles for in vivo tissue marking in surgical, endoscopic or minimally invasive interventions, the method comprising administering to or injecting into a human in need thereof, for in vivo tissue marking in surgical, endoscopic or minimally invasive interventions, the fluorescent nanoparticles, wherein the fluorescent nanoparticles comprise an inorganic core, a passivating layer comprising an imidazole component, and specific ligands, and having a hydrodynamic diameter of the inorganic core with the passivating layer of not more than 15 nm, wherein the nanoparticles show an emission of less than 700 nm.

2. The method as claimed in claim 1, wherein the emission spectrum is from 600 to 650 nm.

3. The method of claim 1, wherein the emission spectrum is from 620 to 650 nm.

4. The method of claim 1, wherein the passivation layer is not more than 10 nm

5. The method of claim 2, wherein the passivation layer is not more than 5 nm.

6. The method of claim 1, wherein the use of nanoparticles for in vivo tissue marking permits differentiating abnormal, pre-carcinogenic or carcinogenic tissue from normal tissue.

7. The method of claim 1, wherein during surgical intervention the nanoparticles are used to assist precise tumor resection.

8. The method as claimed in claim 1, wherein the nanoparticles additionally include at least one modifier.

9. The method as claimed in claim 1, wherein the inorganic core is a cluster essentially comprising noble metal atoms, the cluster having 2 to 27 atoms.

10. The method as claimed in claim 1, wherein the core comprises an alloy selected from the group of the following alloys: CdSeTe, CdSSe, CdSTe, ZnSeTe, ZnCdTe, CdHgS, CdHgTe, InGaAs, GaAlAs, InGaN, InGaP, CdSe or CdTe.

11. The method as claimed in claim 1, wherein the passivating layer comprises at least one compound able to coordinate with a metal atom or metal ion and having a Lewis base function or a heteroaromatic system.

12. The method as claimed in claim 11, wherein the imidazole component comprises one or more compounds selected from the following group consisting of: histidine, carnosine, anserine, baleine, homocarnosine, histidylphenylalanine, cyclo-histidylphenylalanine, 5amino-4-imidazole-carboxamide, histidylleucine, 2-mercaptoimidazole, boc-histidine, hydrazide, histinol, 1-methylhistidine, 3-methylhistidine, imidazolysine, imidazole-containing ornithine, 5-methylimidazole, imidazole-containing alanine (beta)-(2-imidazolyl)-L(alpha)alanine), carzinine, histamine, each of which is either unsubstituted by substituted by reactive amino, thiol, carboxyl or carboxamide groups.

13. The method as claimed in claim 11, wherein the passivating layer comprises a crosslinker for crosslinking the imidazole component.

14. The method as claimed in claim 13, wherein the crosslinking component comprises at least one of an alkylphosphine and an alkylphosphine derivative.

15. The method as claimed in claim 8, wherein the at least one modifier is selected from the group of the following compounds: polyethylene glycol, monosaccharides, disaccharides, trisaccharides, low molecular weight polysaccharides, hydrophilic vitamins, lipophilic vitamins, fatty acids, polyalcohols, Teflon, amino acids, nonspecific peptides or proteins, phosphorylcholine, polylactate and derivatives of said compounds.

16. A method of using fluorescent nanoparticles for in vivo tissue marking in surgical, endoscopic or minimally invasive interventions, the method comprising administering to or injecting into a human in need thereof, for in vivo tissue marking in surgical, endoscopic or minimally invasive interventions, the fluorescent nanoparticles, wherein the fluorescent nanoparticles comprise an inorganic core, a passivating layer comprising an imidazole component, and specific ligands, and having a hydrodynamic diameter of the inorganic core with the passivating layer of not more than 15 nm, said nanoparticles show an emission of less than 700 nm, and wherein marking permits differentiating abnormal, precarcinogenic or carcinogenic tissue from normal tissue.

17. The method as claimed in claim 11, wherein the imidazole component comprises histidylleucine.

18. The method as claimed in claim 1, wherein the core has a homogeneous composition and is characterized by a bandgap energy which is non-linear in relation to the molar ratio of the two semiconductors.

* * * * *